United States Patent
Pae et al.

(10) Patent No.: US 11,915,832 B2
(45) Date of Patent: Feb. 27, 2024

(54) APPARATUS AND METHOD FOR PROCESSING MULTI-OMICS DATA FOR DISCOVERING NEW DRUG CANDIDATE SUBSTANCE

(71) Applicant: MEDIRITA, Seoul (KR)

(72) Inventors: Young Woo Pae, Seoul (KR); Seung-Hyun Jin, Seoul (KR)

(73) Assignee: MEDIRITA, Seoul (KR)

( * ) Notice: Subject to any disclaimer, the term of this patent is extended or adjusted under 35 U.S.C. 154(b) by 430 days.

(21) Appl. No.: 17/288,906

(22) PCT Filed: Mar. 13, 2019

(86) PCT No.: PCT/KR2019/002919
§ 371 (c)(1),
(2) Date: Apr. 26, 2021

(87) PCT Pub. No.: WO2020/138589
PCT Pub. Date: Jul. 2, 2020

(65) Prior Publication Data
US 2021/0398688 A1    Dec. 23, 2021

(30) Foreign Application Priority Data

Dec. 24, 2018  (KR) .................. 10-2018-0168656
Mar. 13, 2019  (KR) .................. 10-2019-0028789

(51) Int. Cl.
*G06F 16/245*    (2019.01)
*G16B 45/00*    (2019.01)
(Continued)

(52) U.S. Cl.
CPC ........... *G16H 50/70* (2018.01); *G06F 16/245* (2019.01); *G06F 16/9024* (2019.01);
(Continued)

(58) Field of Classification Search
None
See application file for complete search history.

(56) References Cited

U.S. PATENT DOCUMENTS

2015/0006445 A1   1/2015   Benz et al.
2015/0262082 A1   9/2015   Vaske et al.
(Continued)

FOREIGN PATENT DOCUMENTS

KR   10-2016-0072842 A   6/2016
KR   10-2016-0084363 A   7/2016
KR   10-2018-0109421 A   10/2018

OTHER PUBLICATIONS

International Search Report for PCT/KR2019/002919 dated Sep. 23, 2019 from Korean Intellectual Property Office.
(Continued)

*Primary Examiner* — Giuseppi Giuliani
(74) *Attorney, Agent, or Firm* — Sughrue Mion, PLLC

(57) ABSTRACT

A method for processing data for discovering a new drug candidate substance by a data processing apparatus includes receiving at least some of omics levels that make up omics through a user interface, receiving at least some types of mutual association degrees among a plurality of types of mutual association degrees, selecting a DB for the at least some of the omics levels and a DB for the at least some types of mutual association from an omics DB including data for each omics level and data for each type of mutual association, generating a first matrix composed of the DB for the at least some of the omics levels and the DB for the at least some types of mutual association degrees, receiving a predetermined search word through the user interface, extracting a plurality of biological entities, and generating a multi-omics network in which a plurality of nodes.

13 Claims, 10 Drawing Sheets

(51) Int. Cl.
  *G06F 16/901*  (2019.01)
  *G16H 50/70*   (2018.01)
  *G16H 70/60*   (2018.01)
  *G16H 70/40*   (2018.01)
  *G16B 40/00*   (2019.01)

(52) U.S. Cl.
  CPC ............ *G16B 40/00* (2019.02); *G16B 45/00* (2019.02); *G16H 70/40* (2018.01); *G16H 70/60* (2018.01)

(56) References Cited

U.S. PATENT DOCUMENTS

| | | | |
|---|---|---|---|
| 2018/0166170 A1* | 6/2018 | Theofilatos | G16B 20/00 |
| 2018/0190381 A1* | 7/2018 | Szeto | G16H 20/10 |
| 2019/0163869 A1* | 5/2019 | Nagarajan | G16B 5/00 |
| 2019/0220524 A1* | 7/2019 | Costabello | G06F 16/24578 |
| 2020/0013480 A1* | 1/2020 | Baliga | G16C 20/50 |
| 2020/0227166 A1* | 7/2020 | Rose | G16H 10/40 |

OTHER PUBLICATIONS

Yu, Y. et al., "PreMedKB: an integrated precision medicine knowledgebase for interpreting relationships between diseases, genes, variants and drugs", Nucleic Acids Research. Nov. 8, 2018 (Eletronic publication), vol. 47, pp. D1090-D1101.

Arrell, D. K. et al., "Network Systems Biology for Drug Discovery", Clinical pharmacology & Therapeutics, Jul. 2010, vol. 88, No. 1, pp. 120-125.

* cited by examiner

○ : NODE
— : EDGE

FIG. 7

| Node | Edge |
|---|---|
| Gene ▽ | interacts ▽ |
| | interacts |
| | participates |
| | covaries |
| | regulates |
| | associates |
| | binds |
| | upregulates |
| | causes |
| | resembles |
| | treats |
| | downregulates |
| | plliates |
| | presents |
| | localizes |
| | includes |
| | expresses |

~160

— : EDGE
● : NODE(Disease)
■ : NODE(Compound)
▲ : NODE(Pathway)
▼ : NODE(Gene)

APPARATUS AND METHOD FOR PROCESSING MULTI-OMICS DATA FOR DISCOVERING NEW DRUG CANDIDATE SUBSTANCE

TECHNICAL FIELD

The present invention relates to an apparatus and method for processing multi-omics data for discovering a new drug candidate substance, and more particularly, to an apparatus and method for processing data for generating a multi-omics network having a hierarchical structure from an omics DB in order to discover the new drug candidate substance.

BACKGROUND ART

It is known that it takes a total of 15 years and costs 2 to 3 trillion won on average to develop a new drug. Most of all, it is known that it takes about 6 years to discover the new drug candidate substance before preclinical trial.

In general, in order to discover the new drug candidate substance, which is a first stage in a pipeline for developing the new drug, a large number of specialized research personnel are going through a process of searching for a huge amount of information one by one and inferring association between major biological entities from this search.

According to the Life Intelligence Consortium (2017) recently launched in Japan, it is predicted that the time required to develop a new drug can be reduced to about 40% and the cost can be reduced to about 50% when artificial intelligence technology is used to develop the new drug.

Meanwhile, omics is also referred to as somatics, is a term referring to all the aggregates of comprehensive biomolecules including genomes, cells, tissues, organs, etc., and examples thereof include genomics, proteomics, metabolomics, etc. FIG. 1 illustrates a hierarchical structure of a human body. Recently, the concept of multi-omics, which means a comprehensive and integrated analysis between different omics levels, is being introduced, and it is necessary to utilize such a multi-omics network in order to develop a new drug with a high hit rate.

However, a specific method for efficiently generating the multi-omics network using omics data has not been developed.

DISCLOSURE OF THE INVENTION

Technical Problem

The technical problem to be solved by the present invention is to provide an apparatus and method for processing data for discovering a new drug candidate substance.

Another technical problem to be solved by the present invention relates to an apparatus and method for generating a multi-omics network from an omics DB (database).

Technical Solution

A method for processing data for discovering a new drug candidate substance by a data processing apparatus according to an embodiment of the present invention includes receiving at least some of omics levels that make up omics through a user interface, receiving at least some types of mutual association degrees among a plurality of types of mutual association degrees that make up the omics through the user interface, selecting a DB for the at least some of the omics levels and a DB for the at least some types of mutual association from an omics DB including data for each omics level and data for each type of mutual association, generating a first matrix composed of the DB for the at least some of the omics levels and the DB for the at least some types of mutual association degrees, receiving a predetermined search word through the user interface, extracting a plurality of biological entities related to the predetermined search word and degrees of mutual associations between the plurality of biological entities from the DB for the at least some of the omics levels and the DB for the at least some types of mutual association degrees, and generating a multi-omics network in which a plurality of nodes including the plurality of biological entities are connected according to the degrees of mutual associations between the plurality of biological entities, and some of the plurality of biological entities are included in different omics levels from the other biological entities.

The method for processing data for discovering the new drug candidate substance may further include generating a graph theory index of the multi-omics network, and extracting some paths having a connection relationship between different omics levels in the multi-omics network by using some nodes extracted using the graph theory index among the plurality of nodes.

The method for processing data for discovering the new drug candidate substance may further include displaying the extracted some paths having the connection relationship between different omics levels in the multi-omics network in a hierarchical structure.

The graph theory index may include at least one of a shortest path between nodes, a clustering coefficient for each node, a centrality coefficient for each node, and a hub characteristic for each node, for a plurality of nodes constituting the multi-omics network.

The plurality of omics levels may include at least some of a gene level, a protein level, a metabolite level, a symptom level, a disease level, a compound level, a drug level, and a side effect level.

The first matrix may be generated such that at least some of the omics levels are disposed on each of a horizontal axis and a vertical axis, and the types of mutual association are displayed at points where the horizontal axis and the vertical axis intersect.

The generating the multi-omics network may include generating a second matrix composed of the plurality of biological entities and the degrees of mutual associations between the plurality of biological entities and connecting the plurality of biological entities with the degrees of mutual associations between the plurality of biological entities, and in the second matrix, the plurality of biological entities may be sequentially disposed on a horizontal axis and a vertical axis according to a hierarchical structure of the omics levels, and the degrees of mutual associations between the plurality of biological entities may be displayed at points where the horizontal axis and the vertical axis intersect.

An apparatus for processing data for discovering a new drug candidate substance according to an embodiment of the present invention includes a user interface unit that receives at least some of omics levels that make up omics and receives at least some types of mutual association degrees among a plurality of types of mutual association degrees that make up the omics, a DB extracting unit that selects a DB for the at least some of the omics levels and a DB for the at least some types of mutual association from an omics DB including data for each omics level and data for each type of mutual association and generates a first matrix composed of the DB for the at least some of the omics levels and the DB for the at least some types of mutual association degrees, and a data generating unit that extracts a plurality of biological entities related to the predetermined search word and degrees of mutual associations between the plurality of biological entities from the DB for the at least some of the omics levels and the DB for the at least some types of mutual association and generates a multi-omics network in which a plurality of nodes including the plurality of biological entities are connected according to the degrees of mutual associations between the plurality of biological entities, and some of the plurality of biological entities are included in different omics levels from the other biological entities.

A recording medium according to an embodiment of the present invention is a recording medium in which a computer-readable program is recorded to execute a method for processing data which includes receiving at least some of omics levels that make up omics through a user interface, receiving at least some types of mutual association degrees among a plurality of types of mutual association degrees that make up the omics through the user interface, selecting a DB for the at least some of the omics levels and a DB for the at least some types of mutual association from an omics DB including data for each omics level and data for each type of mutual association, generating a first matrix composed of the DB for the at least some of the omics levels and the DB for the at least some types of mutual association degrees, receiving a predetermined search word through the user interface, extracting a plurality of biological entities related to the predetermined search word and degrees of mutual associations between the plurality of biological entities from the DB for the at least some of the omics levels and the DB for the at least some types of mutual association degrees, and generating a multi-omics network in which a plurality of nodes including the plurality of biological entities are connected according to the degrees of mutual associations between the plurality of biological entities, and some of the plurality of biological entities are included in different omics levels from the other biological entities.

Advantageous Effects

According to the embodiment of the present invention, refined information about biological entities related to a predetermined search word and a degree of mutual association between the biological entities can be extracted within a short time without searching for a huge amount of information one by one in order to discover a new drug candidate substance.

In particular, according to an embodiment of the present invention, it is possible to obtain a multi-omics network composed of only the omics level and the degree of mutual association desired by the user, it is possible to easily derive the degree of mutual association between biological entities located at different omics levels desired by the user, and accordingly, it is possible to conveniently search a hierarchical structure of the body and the its connection relationship with the conditions, diseases and symptoms externally expressed from the hierarchical structure of the body, and easily understand disease and pharmacological mechanisms.

Accordingly, it is possible to significantly reduce the cost and period required to discover a new drug candidate substance with a high hit rate or a target of the new drug candidate substance.

BRIEF DESCRIPTION OF THE DRAWINGS

FIG. 7 illustrates an example in which a type of mutual association degree is input in step S110 according to an embodiment of the present invention.

MODE FOR CARRYING OUT THE INVENTION

Figure 1:
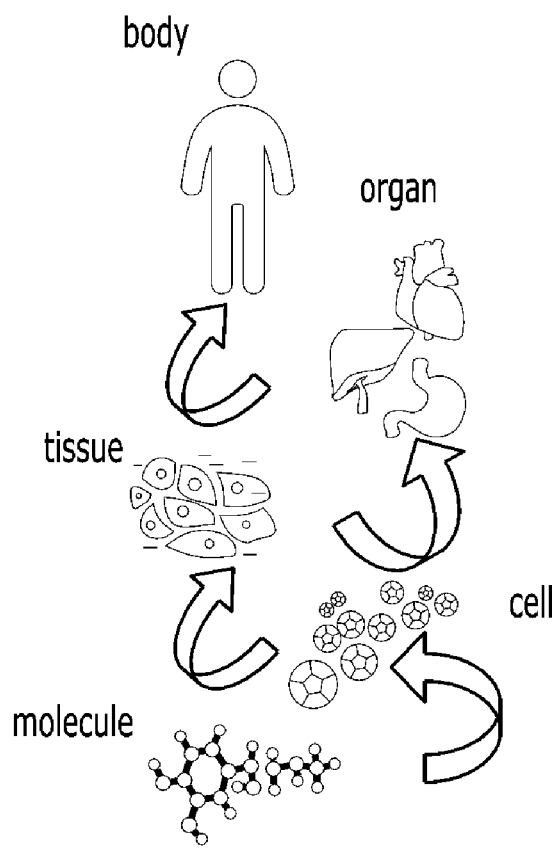
FIG. 1 illustrates a hierarchical structure of a human body.

The present invention can be modified in various ways and may include various embodiments, and thus specific embodiments of the present invention will be described by exemplifying them in the drawings. However, this is not intended to limit the present invention to the specific embodiments and should be understood to cover all changes, equivalents, and substitutes included within the spirit and technical scope of the present invention.

Terms including ordinal numbers such as second and first may be used to describe various components, but the components are not limited by the terms. The above terms are used only for the purpose of distinguishing one component from another component. For example, without departing from the scope of right of the present invention, a second component may be named as a first constitutional element, and similarly, the first component may be named as the second component. The term of and/or includes a combination of a plurality of related listed items or any of the plurality of related listed items.

When a certain component is referred to as being "coupled" or "connected" to another constitutional element, it should be understood that the component may be directly coupled or connected to the other component, but other components may exist in the middle. On the other hand, when a certain component is referred to as being "directly coupled" or "directly connected" to another component, it should be understood that there is no other component in the middle.

The terms used in the present application are only used to describe specific embodiments, and are not intended to limit the present invention. A singular expression includes a plural expression, unless it is explicitly meant differently in the context. In the present application, it is to be understood that terms such as "include" or "have" are intended to designate the existence of features, numbers, steps, actions, components, parts, or combinations thereof described in the specification and do not preclude the possibility of the presence or addition of one or more other features or numbers, steps, actions, components, parts, or combinations thereof.

Unless otherwise defined, all terms used herein including technical or scientific terms have the same meaning as generally understood by a person with ordinary skill in the art to which the present invention pertains. Terms such as those defined in a generally used dictionary, should be interpreted as having a meaning consistent with the meaning in the context of the related technology, and are not to be interpreted as an ideal or excessively formal meaning unless explicitly defined in the present application.

Hereinafter, exemplary embodiments will be described in detail with reference to the accompanying drawings, but identical or corresponding components are denoted by the same reference numerals regardless of reference symbols, and redundant descriptions thereof will be omitted.

Figure 2:
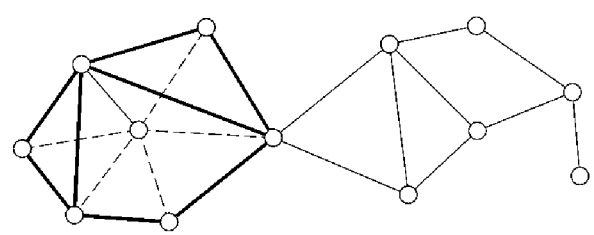
FIG. 2 illustrates a concept of a network.

FIG. 2 illustrates a concept of a network.

Referring to FIG. 2, the network may be composed of a plurality of nodes, and two nodes may be connected by an edge. In this specification, the network may be a knowledge network, a biological network, and a multi-omics network, and the node may represent a biological entity, and the edge may represent a degree of mutual association between two biological entities.

Figure 3:
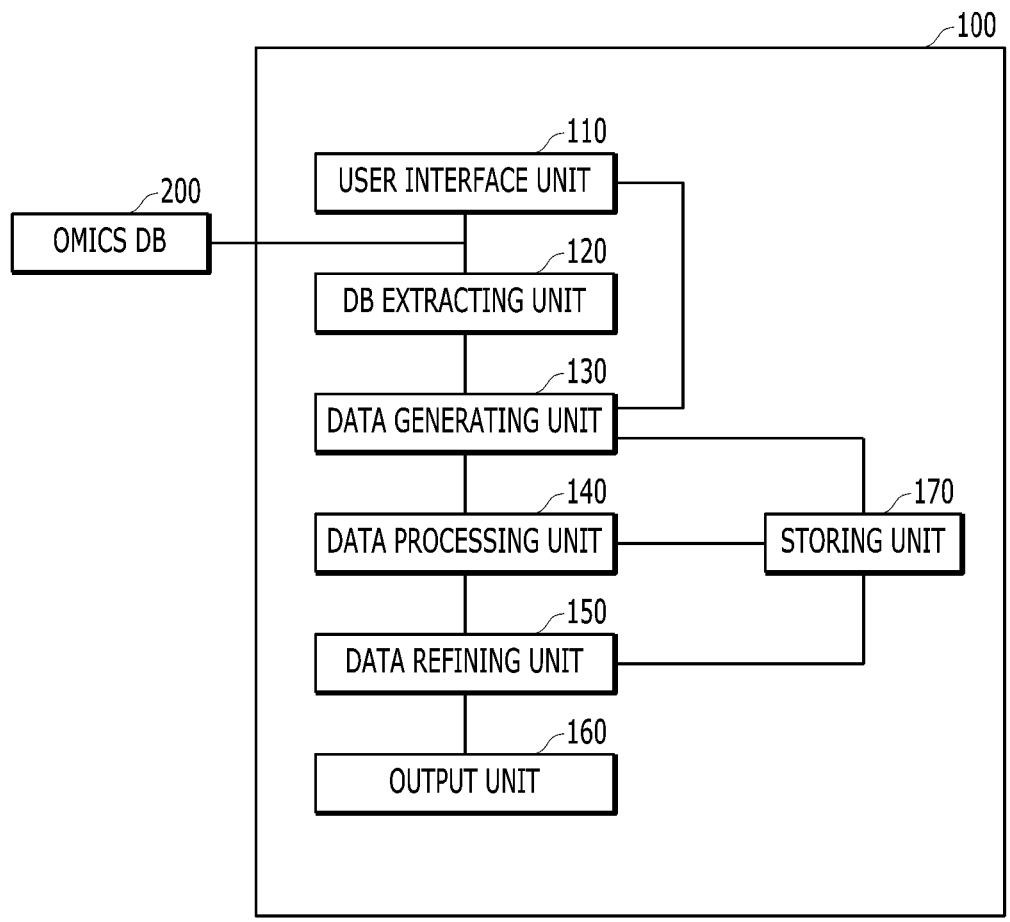
FIG. 3 is a block diagram of an apparatus for processing data for discovering a new drug candidate substance according to an embodiment of the present invention.
Figure 4:
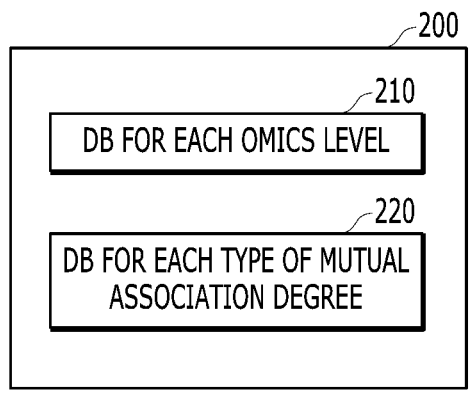
FIG. 4 is a block diagram of an omics DB used by the apparatus for processing data for discovering the new drug candidate substance according to the embodiment of the present invention.
Figure 5:
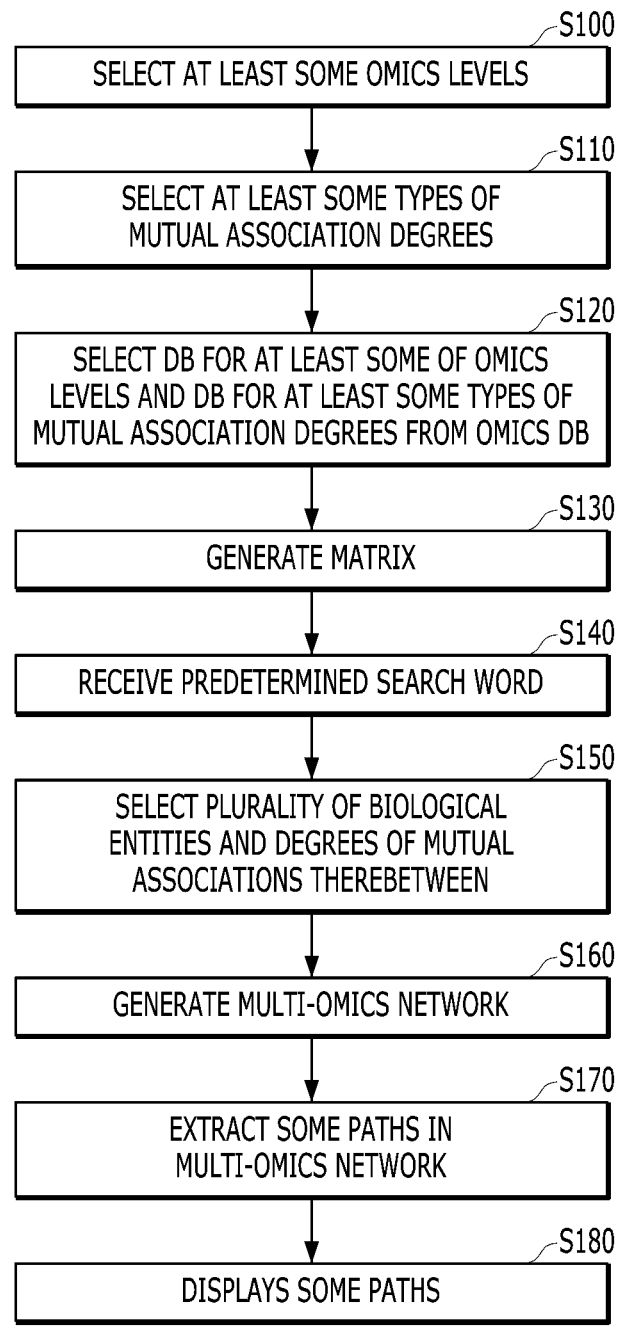
FIG. 5 is a flowchart of a method for processing data for discovering a new drug candidate substance of the apparatus for processing data according to an embodiment of the present invention.

FIG. 3 is a block diagram of an apparatus for processing data for discovering a new drug candidate substance according to an embodiment of the present invention, FIG. 4 is a block diagram of an omics DB used by the apparatus for processing data for discovering the new drug candidate substance according to the embodiment of the present invention, and FIG. 5 is a flowchart of a method for processing data for discovering a new drug candidate substance of the apparatus for processing data according to an embodiment of the present invention.

Referring to FIG. 3, an apparatus for processing data 100 for discovering a new drug candidate substance includes a user interface unit 110, a DB extracting unit 120, a data generating unit 130, a data processing unit 140, and a data refining unit 150, an output unit 160, and a storing unit 170.

Referring to FIGS. 3 to 5, the user interface unit 110 receives at least some of omics levels among a plurality of levels that make up an omics (S100), and receives types of mutual association degrees of at least some of a plurality of types of mutual association degrees that make up the omics (S110). Here, the omics is also referred to as somatics, e.g., there are genetics, transcriptomes, proteomics, metabolomics, epigenetics, geology, etc., and in detail, may include contents related to anatomy, biological process, pathway, pharmacological class, symptoms, diseases, compounds, drugs, side effects, etc., but are not limited thereto. The plurality of omics levels may include a gene level, a transcription level, a protein level, a metabolite level, an epigene level, a lipid level, an anatomy level, a biological process level, a pathway level, a pharmacological class level, a symptom level, a disease level, a compound level, a drug level, a side effect level, etc., but are not limited thereto. Here, an anatomy may mean a tissue, an organ, etc., and the biological process may be a series of events including cellular components, such as location at the level of the structure in cells, and molecular functions extracted from gene ontology, and the pharmacological class may be a pharmacological effect, a mechanism of action. In addition, the plurality of types of mutual association degrees may include "interact", "participate", "covariate", "regulate", "associate", "bind ", "upregulate", "cause", "resemble", "treat", "downregulates", "palliate", "present", "localize", "include", and "express", and an identification number or identification symbol may be arbitrarily assigned for each type. The identification number or identification symbol for each type may be set by a user or may be set automatically.

Figure 6:
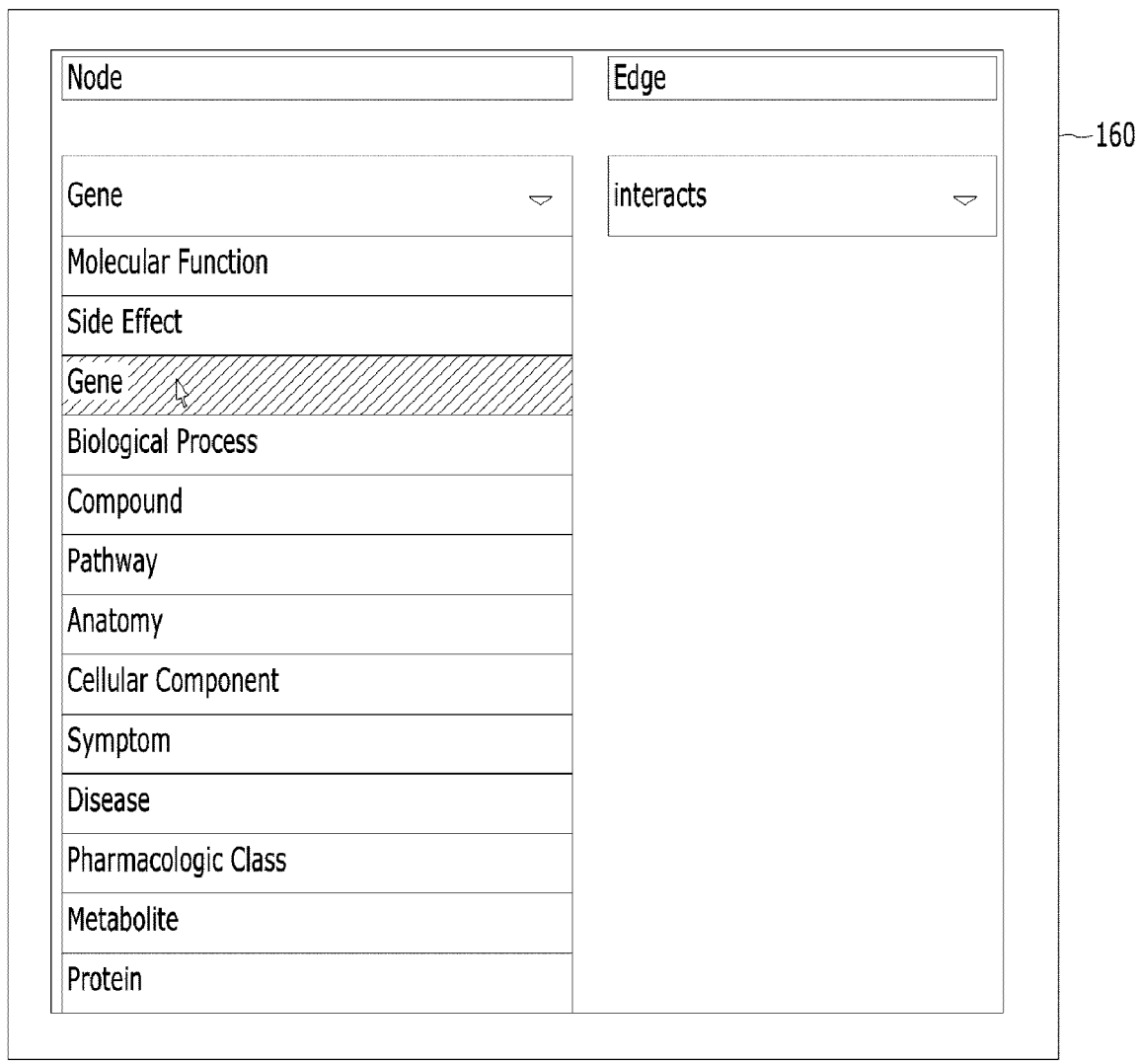
FIG. 6 illustrates an example in which an omics level is input in step S100 according to an embodiment of the present invention.

FIG. 6 illustrates an example in which an omics level is input in step S100 according to an embodiment of the present invention, and FIG. 7 illustrates an example in which a type of mutual association degree is input in step S110 according to an embodiment of the present invention. Referring to FIG. 6, a screen in which the plurality of omics levels can be selected may be exposed through the output unit 160, and at least some of the omics levels may be selected through the user interface unit 110. In addition, referring to FIG. 7, a screen in which a plurality of types of mutual association degrees may be selected may be exposed through the output unit 160, and at least some types of the mutual association degrees may be selected through the user interface unit 110 from among the plurality of types of mutual association degrees.

Next, the DB extracting unit 120 extracts a DB for at least some of the omics levels selected in step S100 and a DB for at least some types of mutual association degrees selected in step S110 from an omics database (DB) (S120). Here, an omics DB 200 may be a big data DB, may be a DB outside the apparatus for processing data 100 according to an embodiment of the present invention, and may be a global public DB that anyone can access or an authenticated person can access under predetermined conditions. The omics DB 200 may store information about an omics level and information about a degree of mutual association between biological entities within the omics level in advance. For example, as illustrated in FIG. 4, the omics DB 200 may include a DB 210 for each omics level and a DB 220 for each type of mutual association degree. The DB 210 for each omics level may include, e.g., a gene DB, a transcription DB, a protein DB, a metabolite DB, an epigene DB, a lipid DB, an anatomy DB, a biological process DB, a pathway DB, a symptom DB, a disease DB, a compound DB, a drug DB, and a side effect DB. In addition, the DB 220 for each type of mutual association degree may include an interaction DB, a participate DB, a covariate DB, a regulate DB, an associate DB, a bind DB, and an upregulate DB, a cause DB, a resemble DB, a treat DB, a downregulates DB, a palliate DB, a present DB, a localize DB, an include DB, and an express DB. These DBs can be managed and operated by being integrated into one big data DB, or managed and operated by being distributed.

Figure 8:
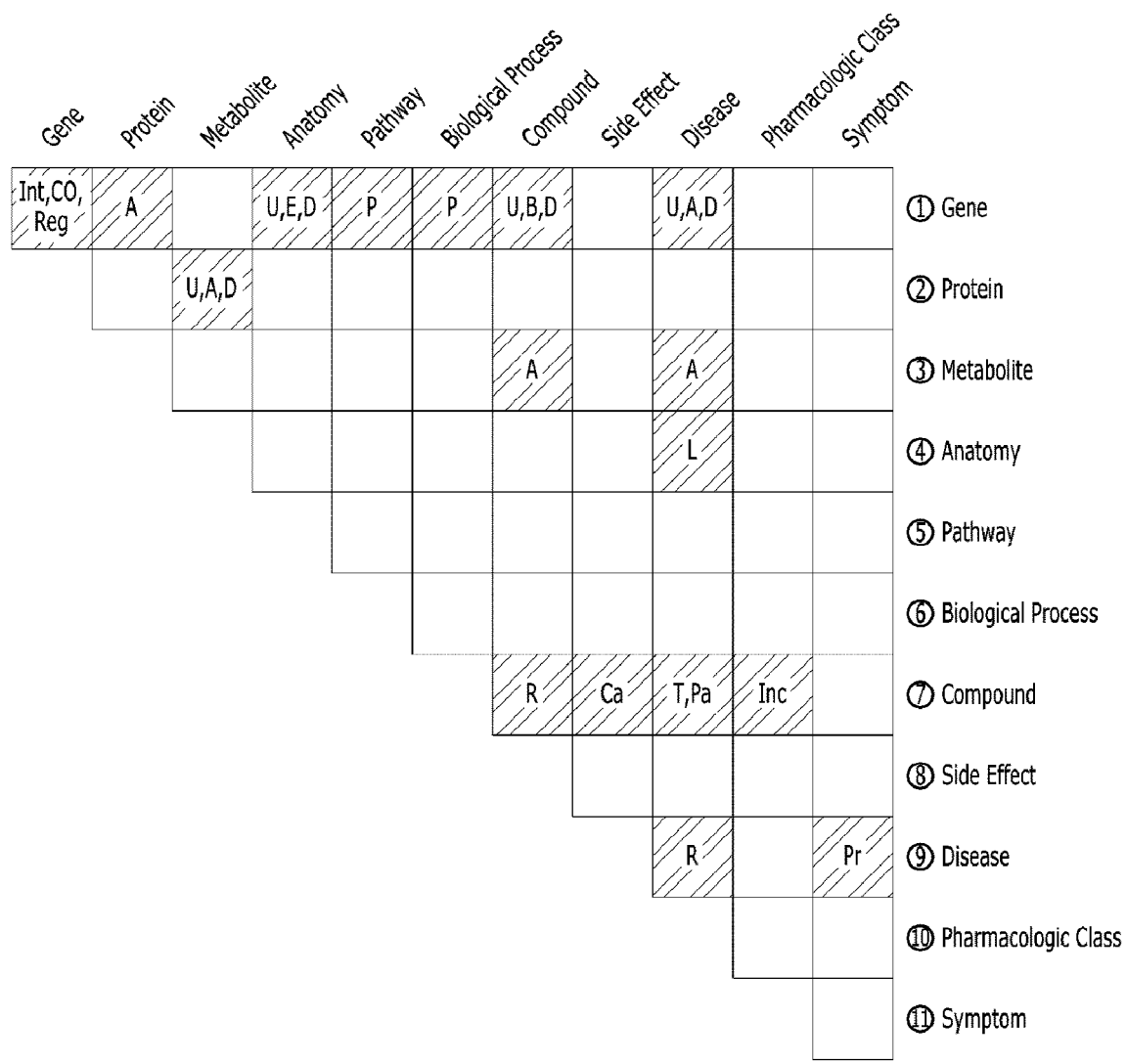
FIG. 8 illustrates an example of a first matrix generated in step S130 according to an embodiment of the present invention.

In addition, the DB extracting unit 120 generates a first matrix composed of a DB for at least some of the omics levels and a DB for at least some types of mutual association degrees extracted in step S120 (S130). Here, the first matrix may be referred to as a set of DBs extracted in step S120. FIG. 8 illustrates an example of the first matrix generated in step S130 according to an embodiment of the present invention. Referring to FIG. 8, the omics levels selected in step S100 are disposed on each of a horizontal axis and a vertical axis, and the types of mutual association degrees selected in step S110 may be generated to be displayed at points where the horizontal and vertical axes intersect. For example, a gene level, a protein level, a metabolite level, an anatomy level, a pathway level, a biological process level, a compound level, a side effect level, a disease level, a pharmacological class level, and a symptom level may be disposed on each of the horizontal axis and vertical axes of the first matrix, and at least one of interact Int, participate P, covariate Co, regulate Reg, association A, bind B, upregulate U, cause Ca, resemble R, treatment T, downregulates D, palliate Pa, present Pr, localize L, include Inc, and express E, which are the types of mutual association degrees, may be displayed at the points where the horizontal axis and the vertical axis intersect.

Figure 9:
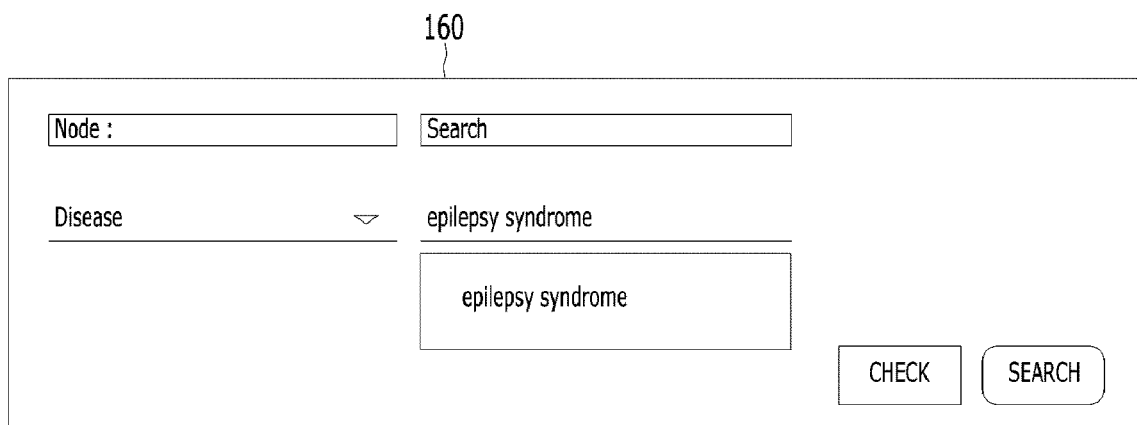
FIG. 9 illustrates an example in which a predetermined search word is input.

Meanwhile, the user interface unit 110 receives a predetermined search word (S140). The predetermined search word may be a search word that the user wishes to search for information, and may include one of a plurality of biological entities included in each omics level, e.g., one of a gene name, a protein name, a metabolite name, a symptom name, a disease name, a compound name, a drug name, and a side effect name. FIG. 9 illustrates an example in which the predetermined search word is input. Referring to FIG. 9, a screen for inputting the predetermined search word may be exposed through the output unit 160, and the predetermined search word may be input through the user interface unit 110. FIG. 9 illustrates an example in which a disease name is selected as a category and epilepsy syndrome is input as the predetermined search word.

Next, the data generating unit 130 extracts at least one biological entity related to the predetermined search word received in step S140 using the first matrix generated in step S130, and extracts the degree of mutual association between the predetermined search word and the extracted biological entity using the first matrix generated in step S130 (S150). Here, the biological entity may include at least one of the gene, the protein, the metabolite, the symptom, the disease, the compound, and the drug, and the omics level to which the predetermined search word belongs may be the same as or different from the omics level to which the biological entity belongs. For example, as illustrated in FIG. 9, when the predetermined search word is epilepsy syndrome, which is a disease name, the biological entities extracted in step S150 may include at least one of the gene associated with epilepsy syndrome, the protein associated with epilepsy syndrome, the metabolite associated with epilepsy syndrome, the symptom associated with epilepsy syndrome, the disease associated with epilepsy syndrome, the compound associated with epilepsy syndrome, and the drug associated with epilepsy syndrome. To this end, the data generating unit 130 may extract the biological entity associated with epilepsy syndrome from each of the gene DB, the protein DB, the metabolite DB, the anatomy DB, the pathway DB, the biological process DB, the compound DB, the side effect DB, the disease DB, the pharmacological class DB, and the symptom DB, that constitute the first matrix, in step S130. Accordingly, the biological entities extracted in step S150 may include at least one of a plurality of genes associated with epilepsy syndrome, a plurality of proteins associated with epilepsy syndrome, a plurality of metabolites associated with epilepsy syndrome, a plurality of symptoms associated with epilepsy syndrome, a plurality of diseases associated with epilepsy syndrome, a plurality of compounds associated with epilepsy syndrome, and a plurality of drugs associated with epilepsy syndrome.

In this way, when extracting the biological entities associated with the predetermined search word and the degrees of mutual associations by using the first matrix in step S130, the amount of DB to be searched can be significantly reduced and accordingly, the time and cost for searching for information can be reduced, and it is possible to extract only the information desired by the user.

In this case, in order for the data generating unit 130 to extract at least one biological entity related to the predetermined search word and the degree of mutual association between the biological entities, the data generating unit 130 may be based on artificial intelligence technology including machine learning and use a natural language processing algorithm. Here, natural language processing refers to various technologies that mechanically analyze language phenomena spoken by humans to make the language phenomena into a form that can be understood by a computer, and express the form that can be understood by the computer in a language that can be understood by humans. To this end, the omics DB 200 may be a language-based DB for each type of biological entity, and may include information reflecting machine learned results and feedback results.

Alternatively, in order for the data generating unit 130 to extract at least one biological entity related to the predetermined search word and the degree of mutual association between the biological entities, the data generating unit 130 may be based on artificial intelligence technology including machine learning, and use a deep neural network algorithm. Here, the deep neural network is an artificial neural network composed of several hidden layers between an input layer and an output layer, and refers to various technologies used for classification, prediction, image recognition, character recognition, etc. To this end, the omics DB 200 may be an image-based DB for each type of biological entity, and may include information reflecting machine learned results and feedback results.

Figure 10:
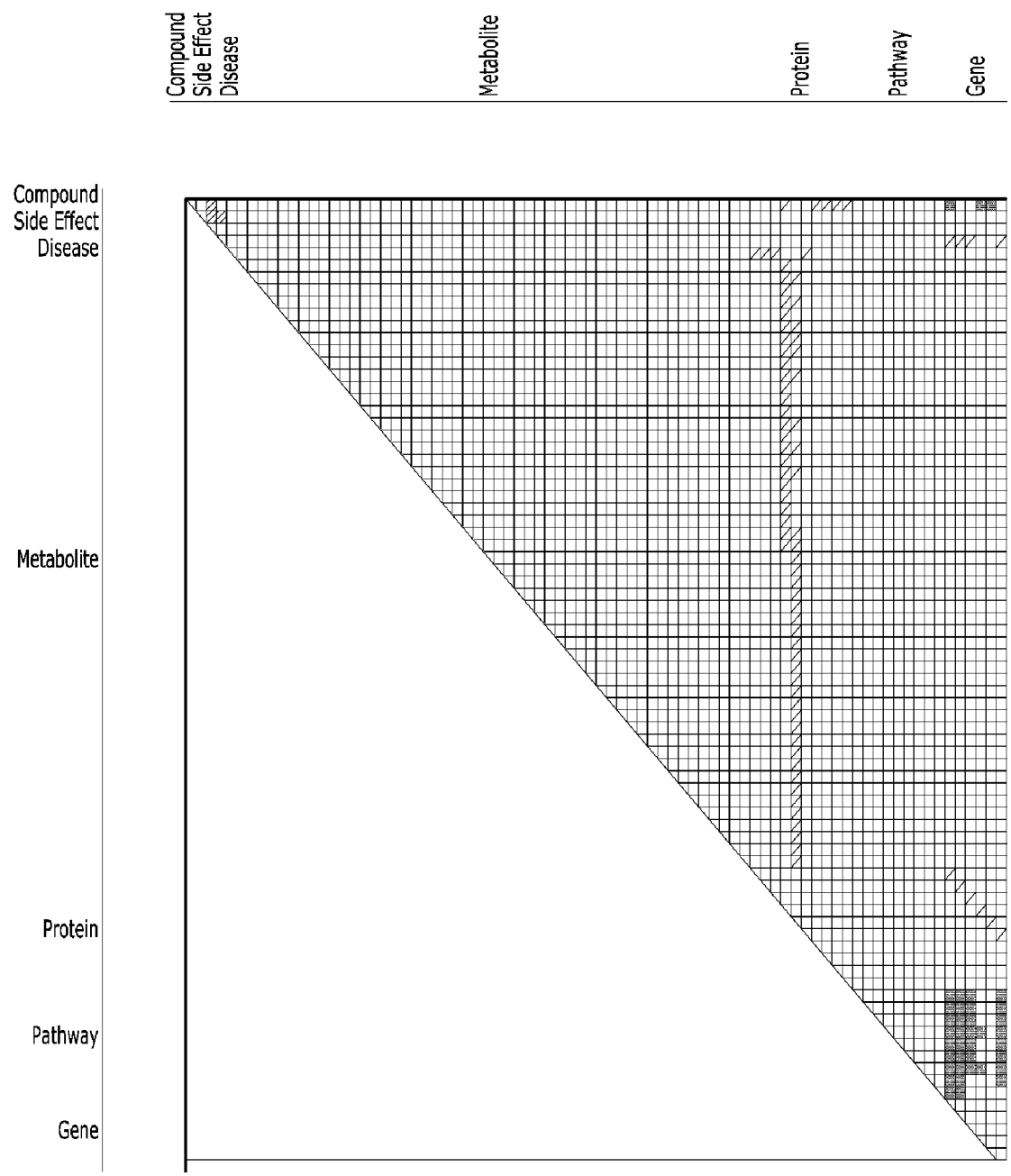
FIG. 10 illustrates a part of an example of a second matrix representing biological entities and degrees of mutual associations between the biological entities extracted in step S150.

FIG. 10 illustrates a part of an example of a second matrix representing biological entities and degrees of mutual associations between the biological entities extracted in step S150. Referring to FIG. 10, the second matrix may be generated in such a way of sequentially disposing a plurality of biological entities on each of the horizontal axis and the vertical axis according to the hierarchical structure of the omics level and displaying the degrees of mutual associations between the plurality of biological entities at points where the horizontal axis and the vertical axis intersect. For example, when the omics level selected in step S100 is the gene level, the pathway level, the protein level, the metabolite level, the disease level, the side effect level, and the compound level, and the predetermined search word input in step S140 is bupropion, which is one of the compounds, it can be seen that a plurality of genes, a plurality of pathways, a plurality of proteins, a plurality of metabolites, a plurality of diseases, a plurality of side effects, and a plurality of compounds, that are associated with bupropion are extracted as biological entities in step S150, and these biological entities are sequentially disposed on each of the horizontal axis and the vertical axis according to the hierarchical structure of the omics levels. In addition, it can be seen that the degrees of mutual associations between the biological entities are displayed in different colors at the points where the horizontal axis and the vertical axis intersect.

The form of the second matrix is illustrative, and is not limited thereto, and may be modified in various forms.

Figure 11:
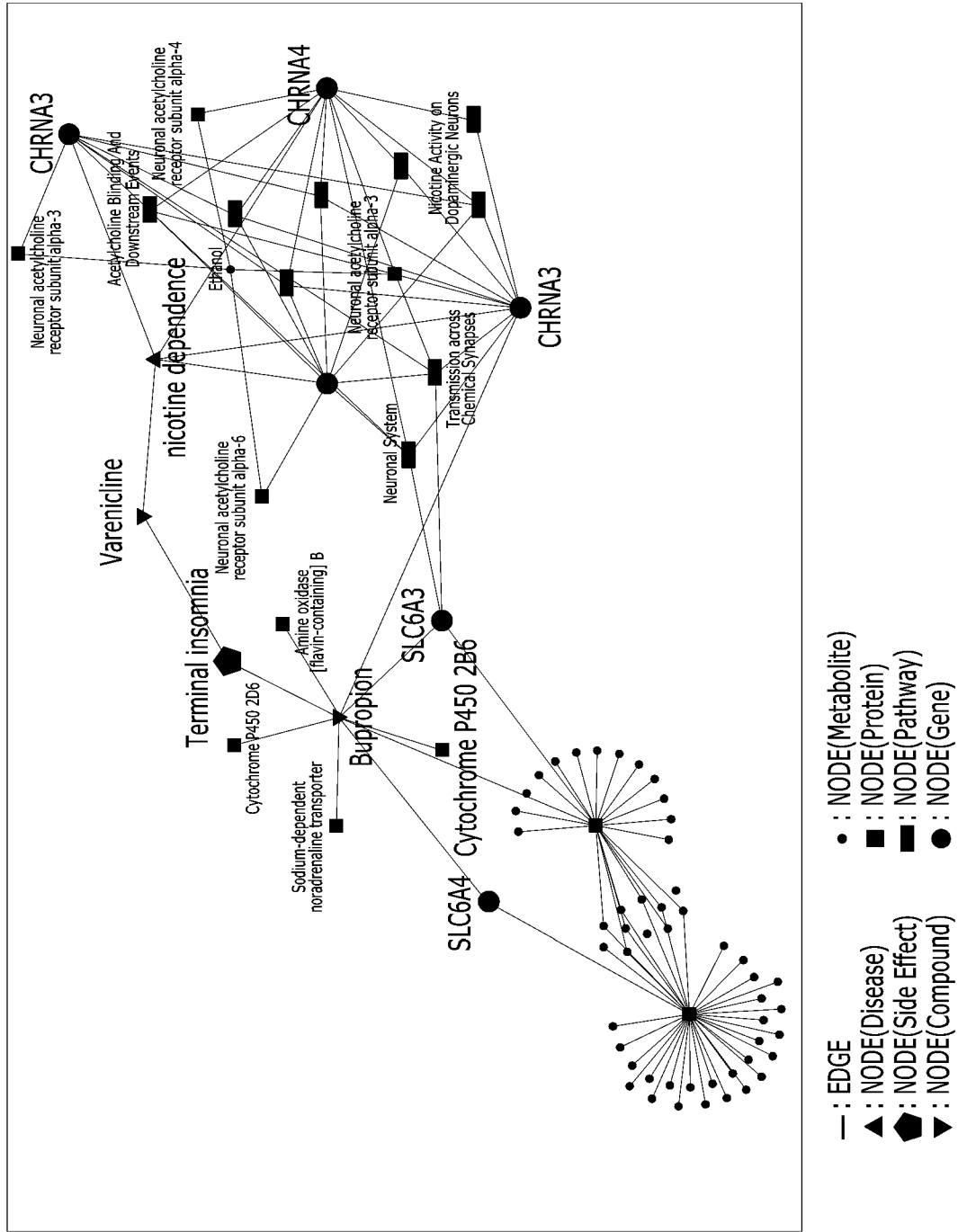
FIG. 11 illustrates an example of a multi-omics network generated according to an embodiment of the present invention.

Next, the data generating unit 130 generates a multi-omics network using the results extracted in step S150 (S160). FIG. 11 illustrates an example of the multi-omics network generated according to an embodiment of the present invention. Here, the multi-omics network may have a form in which a predetermined search word received in step S140 and biological entities extracted in step S150 are used as nodes, and a plurality of nodes are connected using connection lines according to the degrees of mutual associations between the predetermined search word and the biological entities extracted in step S150 or the degrees of mutual associations between the biological entities. Paths from node A, which is one of the nodes in the multi-omics network, to node B, which is other one of the nodes, may vary, and all possible paths may be connected by the connection lines. Here, the multi-omics network is a network composed of the degrees of mutual associations between the biological entities, and may be used interchangeably with a biological network. In the multi-omics network, some of the plurality of biological entities that become the nodes may be included in different omics levels from the other biological entities. That is, as illustrated in FIG. 11, in the multi-omics network, the plurality of biological entities included in the different omics levels such as the gene level, the pathway level, the protein level, the metabolite level, the compound level, the side effect level, and the disease level are used as nodes, and some of the plurality of biological entities included in the gene level may be connected to some of the plurality of biological entities included in the protein level or connected to some of the plurality of biological entities included in the pathway level. Similarly, some of the plurality of biological entities included in the compound level may be connected to some of the plurality of biological entities included in the protein level, connected to some of the plurality of biological entities included in the pathway level, or connected to some of the plurality of biological entities included in the side effect level.

As described above, according to an embodiment of the present invention, when some of the plurality of omics levels and some of the plurality of types of mutual association degrees are received through the user interface unit 110, since the DB for the corresponding omics level and the DB for the type of mutual association degree are automatically extracted, the amount of information to be searched by the apparatus for processing data 100 can be significantly reduced, and accordingly, it is possible to obtain the multi-omics network composed of the omics level and the type of mutual association degree desired by the user. In addition, according to an embodiment of the present invention, when some of the plurality of omics levels and some of the plurality of types of mutual association degree are received through the user interface unit 110, the multi-omics network composed of the omics levels and the types of mutual association degrees desired by the user can be obtained, and accordingly, it is possible to easily grasp the hierarchical structure between the plurality of biological entities associated with the predetermined search word within the omics level desired by the user.

Figure 12:
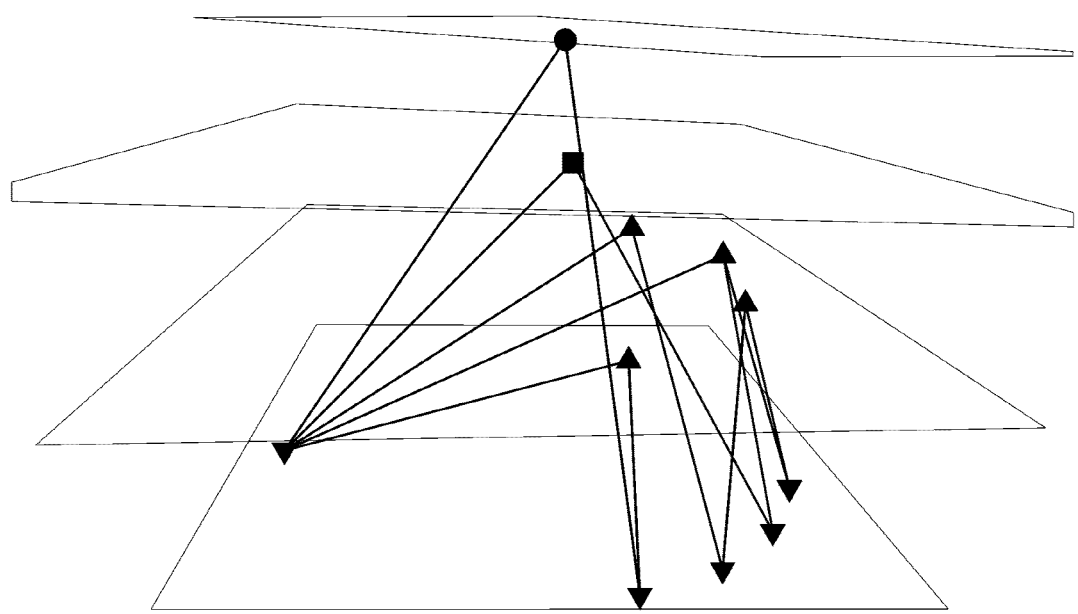
FIG. 12 illustrates an example of some of paths displayed in step S180 according to an embodiment of the present invention.

Next, the data refining unit 150 extracts some paths in the multi-omics network generated in step S160 (S170), and the output unit 160 displays some paths extracted in step S170 (S180). Here, some paths may be paths connecting some nodes extracted from the biological entities in the multi-omics network, the paths may be paths determined to have a relatively high degree of mutual association with the predetermined search word or paths determined to be of relatively high importance among a plurality of paths connecting the biological entities in the multi-omics. FIG. 12 illustrates an example of some paths displayed in step S180 according to an embodiment of the present invention. Referring to FIG. 12, some paths having a connection relationship between different omics levels in the multi-omics may be displayed in a hierarchical structure. Accordingly, it is possible to intuitively grasp the degrees of mutual associations between the plurality of biological entities included in different omics levels.

Meanwhile, in order to extract some paths in the multi-omics network as in step S170, the data processing unit 140 may generate graph theory indexes of the multi-omics network, and the data refining unit 150 may extract some nodes in the multi-omics network having high mutual association in terms of the graph theory indexes generated by the data processing unit 140.

To this end, the graph theory indexes may include at least one of a shortest path between nodes, a clustering coefficient for each node, a centrality coefficient for each node, and a hub characteristic for each node, for a plurality of nodes constituting the multi-omics network.

The shortest path between nodes may mean the shortest path among a large number of paths from node A to node B in the multi-omics network. Hereinafter, a method of calculating the shortest path between node A, which is one of the biological entities, and node B, which is the other of the biological entities, will be described.

There are various paths from node A to node B, and node A and node B may be directly connected, or at least one intermediate node may exist on each path between node A and node B.

The shortest path between node A and node B can be obtained by using the number of intermediate nodes for each path. For example, among various paths between node A and node B, a path with a smaller number of intermediate nodes may be determined to be a shorter path.

Or, the shortest path between node A and node B may be obtained using the number of intermediate nodes for each path, but may reflect a type of mutual association for each connection line. That is, weights may be set differently for each category of mutual association, and the weights may also be applied to mutual association that exists for each path.

Equation 1 is an example of an equation for calculating the shortest path between nodes.

$$d_{i,j}^W = \sum\nolimits_{w_{st} \in g_{i \to j}^w} f(w_{st})  \qquad [\text{Equation 1}]$$

Here, $w_{st}$ is a mutual association index between two nodes s and t, f is a weight transformation function, and $$g_{i \to j}^w$$

is the shortest path between two nodes i and j. A value of Equation 1 is obtained for each path, and a path having the lowest value or the highest value may be selected as the shortest path.

Next, the clustering coefficient for each node may be computed by Equation 2 and Equation 3. Here, the clustering coefficient may be referred to as a grouping coefficient, and may mean a probability that a specific node and neighboring nodes are connected to each other or a connection density between the specific node and neighboring nodes.

$$t_i^w = \frac{1}{2} \sum\nolimits_{j,h \in N} w_{ij} w_{ih} w_{jh}  \qquad [\text{Equation 2}]$$

Here, $t_i^w$ means the number of triangles in a graph created around each node i of the multi-omics network, N is the total set of nodes in the multi-omics network, $w_{ij}$ is a mutual association index between two nodes i and j, $w_{ih}$ is a mutual association index between nodes i and h, and $w_{jh}$ is a mutual association index between two nodes j and h.

$$C^w = \frac{1}{n}\sum_{k \in N} \frac{2t_i^w}{k_i(k_i - 1)} \qquad \text{[Equation 3]}$$

Here, $C^w$ means the clustering coefficient, $t_i^w$ is the number of triangles in the graph created around each node i of the multi-omics network, and $k_i$ means a degree of node i, that is, a value of the degree of connectivity of node i in the multi-omics network.

Next, the centrality index for each node is an index of whether a specific node has the function of a hub, and may be expressed by a $D_{nodal}$ (nodal degree) value, a betweenness centrality (BC) value, a $E_{nodal}$ (nodal efficiency) value, etc. Here, the $D_{nodal}$ value is a value of the degree of connectivity of each node in the multi-omics network, that is, an index indicating how strong or weak node i has connectivity in the multi-omics network, the $E_{nodal}$ value is a value of a degree of efficiency of node i in the multi-omics network, that is, a value expressed as the reciprocal of the shortest path of Equation 1, and is a value with higher efficiency as the path is shorter, and the BC value is an index indicating the number of times that node i becomes a shortcut in the path between nodes in multi-omics network.

First, the $D_{nodal}$ value may be computed by Equation 4.

$$D_{nodal}(i) = \Sigma_{j \in N} w_{ij} \qquad \text{[Equation 4]}$$

Here, $w_{ij}$ is a mutual association index between two nodes i and j, and N is a total set of nodes in the multi-omics network.

In addition, the $E_{nodal}$ value may be computed by Equation 5.

$$E_{nodal}(i) = \sum_{j \in N, j \neq i} \frac{1}{d_{i,j}^w} \qquad \text{[Equation 5]}$$

Here, N is a total set of nodes of the multi-omics network, and $d_{i,j}^w$ is a value indicating the shortest path computed by Equation 1.

Next, Betweenness centrality (BC) may be computed by Equation 6.

$$BC(i) = \sum_{\substack{h,j \in N \\ h \neq j, h \neq i, j \neq i}} \frac{g_{hj}(i)}{g_{hj}} \qquad \text{[Equation 6]}$$

Here, $g_{hj}$ means the shortest distance between nodes h and j, and $g_{hj}(i)$ means the shortest distance between h and j passing through node i.

Next, when it is determined that a predetermined node has a function of a hub, characteristics of the hub are classified. In this case, the characteristics of the hub may be classified into a kinless hub, a connector hub, a provincial hub, etc. Here, the kinless hub means a hub with the most influential hub, that is, a hub connected to nodes in many modules, the connector hub means a hub that connects modules in the knowledge network, and the provincial hub means a hub that has a high influence mainly within the module. Here, the module may be a structural configuration group obtained by subdividing the entire multi-omics network.

To this end, a modularity in the multi-omics network can be computed as in Equation 7. The modularity means the number of module types in the entire multi-omics network.

$$Q^W = \frac{1}{l^W}\sum_{k,j \in N}\left[w_{ij} - \frac{k_i^W k_j^W}{l^W}\right]\delta_{mi,mj} \qquad \text{[Equation 7]}$$

Here, $k_i^n = \Sigma_{j \in N} w_{ij}$ means the sum of weights at node i, and $l^w = \Sigma_{i,j \in N} w_{ij}$ means the sum of weights. $\delta_{mi,mj}$ is the kronecker delta, 1 for mi=mj, and 0 for the rest.

Next, the participation coefficient (PC) of the multi-omics network module may be computed as in Equation 8.

$$PC_i = 1 - \sum_{m \in M}\left(\frac{k_i^w(m)}{k_i^w}\right)^2 \qquad \text{[Equation 8]}$$

Here, M means a set of modules, $k_i^w(m_i)$ means the number of connections between node i and all other nodes in module m, and module m means a structural group obtained by subdividing the entire multi-omics network.

In addition, a z score (within-module degree) of the multi-omics network module may be computed as in Equation 9.

$$z_i^W = \frac{k_i^w(m_i) - \overline{k}^w(m_i)}{\sigma_k^W(m_i)} \qquad \text{[Equation 9]}$$

Here, $m_i$ means node i in module m, $k_i^w(m_i)$ means the degree of connectivity in module m of node i, and $\overline{k}^w(m_i)$ and $\sigma_k^w(m_i)$ refer to the mean and standard deviation of the degree distribution of connectivity within module m, respectively.

Through the computation of the indexes in Equation 9 above, it is possible to distinguish whether each node is a hub or not within the module. For example, as follows, when the Z score of the multi-omics network module is 2.5 or higher, the node may be determined as a hub.

1. within-module z-score ≥2.5: hub
2. within-module z-score <2.5: not hub

In addition, when it is determined that the node is a hub in the module, a type of the hub can be classified as follows through the computation of the indexes in Equation 8, and FIG. 7 illustrates an example of classifying the types of the hub according to PCs.

1. Provincial hub: PC≤0.30
2. Connector hub: 0.3<PC≤0.75
3. Kinless hub: PC>0.75

In this case, the nodes constituting some nodes extracted in step S170 may be some nodes of which at least a part of an index value for the shortest path between nodes, an index value for the clustering coefficient for each node, and an index value for the centrality coefficient for each node is equal to or greater than a threshold value, among the plurality of nodes constituting the multi-omics network in S160. That is, some nodes extracted in step S170 may be generated in such a way of deleting the nodes of which at least a part of the index value for the shortest path between nodes, the index value for the clustering coefficient for each node, and the index value for the centrality coefficient for each node is less than the threshold value among the plurality of nodes constituting the multi-omics network and deleting the connections associated with the deleted nodes.

Here, the graph theory index compared to the threshold value may be each of the index value for the shortest path between nodes, the index value for the clustering coefficient for each node, and the index value for the centrality coefficient for each node. Alternatively, the graph theory index compared to the threshold value may be a value calculated by integrating at least two of the index value for the shortest path between nodes, the index value for the clustering coefficient for each node, and the index value for the centrality coefficient for each node.

In this case, at least one of the index value for the shortest path between nodes, the index value for the clustering coefficient for each node, and the index value for the centrality coefficient for each node may be computed as a standard score for each node, and the computed standard score may be compared with the threshold value.

Here, the standard score may be the z score, and the threshold value may mean 95% of significance.

The Z score can be computed as in Equation 10.

$$z = \frac{X - \text{mean}(x)}{SE(x)} \quad \text{[Equation 10]}$$

Here, z is the z score, X is an index value of a predetermined graph theory index for a specific node in the multi-omics network, mean(x) is an average index value of predetermined graph theory indexes for a plurality of nodes in the multi-omics network, and SE(x) is a standard error of the index value of the predetermined graph theory index in the multi-omics network. Here, it can be expressed as $SE=\sigma/\sqrt{n}$, where $\sigma$ is the standard deviation, and n is the number of nodes constituting the multi-omics network.

That is, the z score may be a value obtained by dividing the difference between the index value of the predetermined graph theory index for each node constituting the multi-omics network and the average index value of the predetermined graph theory index for the plurality of nodes constituting the multi-omics network by the standard error.

In this case, the z score may be computed through a permutation test. The permutation test may be performed by randomly mixing all connection lines constituting the multi-omics network and then computing the z score for each node. In this case, the number of times of random mixing of the connection lines may be 1000 times or more.

Or, the nodes constituting some paths extracted in step S170 may be some nodes extracted by using the index value for the hub characteristic for each node from among the plurality of nodes constituting the multi-omics network. That is, the node constituting some paths extracted in step S170 may be a node determined to be a hub within the module through the computation of the index of Equation 9, preferably a node classified as one of the kinless hub, the connector hub, and the provincial hub, more preferably a node classified as one of the kinless hub and the connector hub, and more preferably, a node classified as the kinless hub.

Meanwhile, the apparatus for processing data 100 according to an embodiment of the present invention may include the data storing unit 170. The data storing unit 170 may be connected to the data generating unit 130, the data processing unit 140, and the data refining unit 150, and may store results calculated from the data generating unit 130, the data processing unit 140, and the data refining unit 150. The data storing unit 170 may be connected to an external learning server in a wired or wirelessly manner, and may transmit stored data to the external learning server.

The term '~unit' used in this embodiment means software or hardware components such as field-programmable gate array (FPGA) or ASIC, and '~unit' performs certain roles. However, the '~unit' is not limited to software or hardware. The '~unit' may be configured to be located in an addressable storage medium, or may be configured to reproduce one or more processors. Accordingly, as an example, the '-unit' includes components such as software components, object-oriented software components, class components, and task components, processes, functions, attributes, procedures, subroutines, segments of program code, drivers, firmware, microcode, circuits, data, databases, data structures, tables, arrays, and variables. Components and functions provided in the '~units' may be combined into a smaller number of components and '~units', or may be further separated into additional components and '~units'. In addition, components and '~units' may be implemented to play one or more CPUs in a device or a security multimedia card.

In the description above, although description has been made with reference to preferred embodiments of the present invention, those skilled in the art will appreciate that various modifications and changes may be made to the present invention within a range not departing from the spirit and scope of the present invention set forth in the following claims.

The invention claimed is:

1. A method for processing data for discovering a new drug candidate substance by a data processing apparatus, the method comprising:
   receiving, through a user interface, one or more omics levels from among a plurality of omics levels that make up omics in an omics database (DB);
   receiving, through the user interface, one or more types of mutual association degrees from among a plurality of types of mutual association degrees that make up the omics in the omics DB;
   selecting, from the omics DB, a first DB for the one or more omics levels and a second DB for the one or more types of mutual association degrees, the first DB including first data about each omics level of the one or more omics levels, and the second DB including second data about each type of mutual association degree of the one or more types of mutual association degrees;
   generating a first matrix composed of the first DB and the second DB, the first matrix having the one or more omics levels disposed on each of a horizontal axis and a vertical axis and the one or more types of mutual association degrees displayed at points where the horizontal axis and the vertical axis intersect;
   receiving, through the user interface, a predetermined search word;
   extracting, using the first matrix, a plurality of biological entities related to the predetermined search word and degrees of mutual associations between the plurality of biological entities which are related to the predetermined search word; and
   generating a multi-omics network in which a plurality of nodes including the plurality of biological entities are connected according to the degrees of mutual associations between the plurality of biological entities,
   wherein a portion of the plurality of biological entities are included in different omics levels from remaining biological entities of the plurality of biological entities.

2. The method of claim 1, further comprising:
generating a graph theory index of the multi-omics network; and
extracting one or more paths having a connection relationship between the different omics levels in the multi-omics network by using one or more nodes extracted from among the plurality of nodes using the graph theory index.

3. The method of claim 2, further comprising:
displaying the extracted one or more paths having the connection relationship between the different omics levels in the multi-omics network in a hierarchical structure.

4. The method of claim 2,
wherein the graph theory index includes at least one of a shortest path between nodes of the plurality of nodes, a clustering coefficient for each node of the plurality of nodes, a centrality coefficient for each node of the plurality of nodes, and a hub characteristic for each node of the plurality of nodes constituting the multi-omics network.

5. The method of claim 1,
wherein the plurality of omics levels include at least one of a gene level, a protein level, a metabolite level, a symptom level, a disease level, a compound level, a drug level, and a side effect level.

6. The method of claim 5, wherein the generating of the multi-omics network comprises:
generating a second matrix composed of the plurality of biological entities and the degrees of mutual associations between the plurality of biological entities; and
connecting the plurality of biological entities with the degrees of mutual associations between the plurality of biological entities, and
wherein, in the second matrix, the plurality of biological entities are sequentially disposed on the horizontal axis and the vertical axis according to a hierarchical structure of the plurality of omics levels, and the degrees of mutual associations between the plurality of biological entities are displayed at points where the horizontal axis and the vertical axis intersect.

7. An apparatus for processing data for discovering a new drug candidate substance, the apparatus comprising:
a memory storing instructions; and
one or more processors configured to execute the instructions to:
receive one or more omics levels from among a plurality of omics levels that make up omics in an omics database (DB) and one or more types of mutual association degrees from among a plurality of types of mutual association degrees that make up the omics in the omics DB;
select, from the omics DB, a first DB for the one or more omics levels and a second DB for the one or more types of mutual association degrees, the first DB including first data about each omics level of the one or more omics levels, and the second DB including second data about each type of mutual association degree of the one or more types of mutual association degrees;
generate a first matrix composed of the first DB and the second DB, the first matrix having the one or more omics levels disposed on each of a horizontal axis and a vertical axis and the one or more types of mutual association degrees displayed at points where the horizontal axis and the vertical axis intersect;
extract, from the first matrix, a plurality of biological entities related to a predetermined search word and degrees of mutual associations between the plurality of biological entities which are related to the predetermined search word; and
generate a multi-omics network in which a plurality of nodes including the plurality of biological entities are connected according to the degrees of mutual associations between the plurality of biological entities,
wherein a portion of the plurality of biological entities are included in different omics levels from remaining biological entities of the plurality of biological entities.

8. The apparatus of claim 7, wherein the one or more processors are further configured to execute the instructions to:
generate a graph theory index of the multi-omics network; and
extract one or more paths having a connection relationship between the different omics levels in the multi-omics network by using one or more nodes extracted from the plurality of nodes using the graph theory index.

9. The apparatus of claim 8, wherein the one or more processors are further configured to execute the instructions to:
display the extracted one or more paths having the connection relationship between the different omics levels in the multi-omics network in a hierarchical structure.

10. The apparatus of claim 8,
wherein the graph theory index includes at least one of a shortest path between nodes of the plurality of nodes, a clustering coefficient for each node of the plurality of nodes, a centrality coefficient for each node of the plurality of nodes, and a hub characteristic for each node of the plurality of nodes constituting the multi-omics network.

11. The apparatus of claim 7,
wherein the plurality of omics levels include at least one of a gene level, a protein level, a metabolite level, a symptom level, a disease level, a compound level, a drug level, and a side effect level.

12. The apparatus of claim 7, wherein the one or more processors are further configured to execute the instructions to:
generate a second matrix composed of the plurality of biological entities and the degrees of mutual associations between the predetermined search word and the plurality of biological entities; and
connect the plurality of biological entities with the degrees of mutual associations between the plurality of biological entities, and
wherein, in the second matrix, the plurality of biological entities are sequentially disposed on the horizontal axis and the vertical axis according to a hierarchical structure of the plurality of omics levels, and the degrees of mutual associations between the plurality of biological entities are displayed at points where the horizontal axis and the vertical axis intersect.

13. A non-transitory recording medium in which a computer-readable program is recorded in order to execute a data processing method which includes:
receiving, through a user interface, one or more omics levels from among a plurality of omics levels that make up omics in an omics database (DB);

receiving, through the user interface, one or more types of mutual association degrees from among a plurality of types of mutual association degrees that make up the omics in the omics DB;

selecting, from the omics DB, a first DB for the one or more omics levels and a second DB for the one or more types of mutual association degrees, the first DB including first data about each omics level of the one or more omics levels, and the second DB including second data about each type of mutual association degree of the one or more types of mutual association degrees;

generating a first matrix composed of the first DB and the second DB, the first matrix having the one or more omics levels disposed on each of a horizontal axis and a vertical axis and the one or more types of mutual association degrees displayed at points where the horizontal axis and the vertical axis intersect;

receiving, through the user interface, a predetermined search word;

extracting, from the first matrix, a plurality of biological entities related to the predetermined search word and degrees of mutual associations between the plurality of biological entities which are related to the predetermined search word; and generating a multi-omics network in which a plurality of nodes including the plurality of biological entities are connected according to the degrees of mutual associations between the plurality of biological entities, wherein a portion of the plurality of biological entities are included in different omics levels from remaining biological entities of the plurality of biological entities.

* * * * *